United States Patent
Euteneuer et al.

(10) Patent No.: US 10,226,325 B2
(45) Date of Patent: Mar. 12, 2019

(54) MEDICAL DEVICE DELIVERY SYSTEM AND METHOD

(71) Applicant: Rotation Medical, Inc., Plymouth, MN (US)

(72) Inventors: Charles L. Euteneuer, St. Michael, MN (US); Rebecca McCarville, Spring Park, MN (US); Duane Frion, Brooklyn Center, MN (US); Nathaniel Zenz-Olson, Blaine, MN (US)

(73) Assignee: Rotation Medical, Inc., Plymouth, MN (US)

( * ) Notice: Subject to any disclaimer, the term of this patent is extended or adjusted under 35 U.S.C. 154(b) by 0 days.

(21) Appl. No.: 14/883,170

(22) Filed: Oct. 14, 2015

(65) Prior Publication Data

US 2016/0030157 A1    Feb. 4, 2016

Related U.S. Application Data

(63) Continuation of application No. 12/729,029, filed on Mar. 22, 2010, now Pat. No. 9,179,910.
(Continued)

(51) Int. Cl.
*A61F 2/08* (2006.01)
*A61B 17/064* (2006.01)
*A61B 17/068* (2006.01)
*A61B 17/00* (2006.01)
*A61B 17/072* (2006.01)
(Continued)

(52) U.S. Cl.
CPC ...... *A61F 2/0805* (2013.01); *A61B 17/00234* (2013.01); *A61B 17/064* (2013.01); *A61B 17/068* (2013.01); *A61B 17/07292* (2013.01); *A61B 17/1155* (2013.01); *A61B 2017/00349* (2013.01); *A61B 2017/0647* (2013.01); *A61B 2017/22038* (2013.01); *A61B 2017/22044* (2013.01); *A61B 2017/22047* (2013.01); *A61F 2/08* (2013.01)

(58) Field of Classification Search
CPC ..................................................... A61F 2/0805
See application file for complete search history.

(56) References Cited

U.S. PATENT DOCUMENTS

| 511,238 A | 12/1893 | Hieatzman |
| 765,793 A | 7/1904 | Ruckel |

(Continued)

FOREIGN PATENT DOCUMENTS

| CA | 2390508 A1 | 5/2001 |
| EP | 0142225 A1 | 5/1985 |

(Continued)

OTHER PUBLICATIONS

Abbaroodle et al., "Rotator Cuff Tear," Wikipedia, pp. 1-14, Web. Dec. 6, 2012.
(Continued)

*Primary Examiner* — Jacqueline Woznicki
(74) *Attorney, Agent, or Firm* — Seager, Tufte & Wickhem LLP

(57) ABSTRACT

A tendon repair implant delivery system and methods incorporating a guide member having a temporary fixation member on or adjacent to the distal end. The point of fixation defines a target site for placement of the tendon repair implant which is subsequently affixed to the tendon.

9 Claims, 7 Drawing Sheets

Related U.S. Application Data

(60) Provisional application No. 61/162,234, filed on Mar. 20, 2009.

(51) Int. Cl.
    *A61B 17/115* (2006.01)
    *A61B 17/22* (2006.01)

(56) References Cited

U.S. PATENT DOCUMENTS

| | | | |
|---|---|---|---|
| 1,728,316 A | 9/1929 | Von Wachenfeldt |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A * | 5/1992 | Eberbach | A61B 17/0057 602/76 |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,211,650 A * | 5/1993 | Noda | A61B 17/0469 289/1.2 |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A * | 4/1994 | Green | A61F 2/0063 604/13 |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |

(56) References Cited

U.S. PATENT DOCUMENTS

| | | |
|---|---|---|
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | DiPoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 * | 7/2002 | Knodel ............... A61B 17/064 606/139 |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |

(56) References Cited

U.S. PATENT DOCUMENTS

| | | |
|---|---|---|
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 8,668,718 B2 | 3/2014 | Euteneuer et al. |
| 8,763,878 B2 | 7/2014 | Euteneuer et al. |
| 8,821,536 B2 | 9/2014 | Euteneuer et al. |
| 9,179,910 B2 | 11/2015 | Euteneuer et al. |
| 9,179,961 B2 | 11/2015 | Euteneuer et al. |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1* | 4/2003 | Naimark .......... A61B 17/00234 604/891.1 |
| 2003/0212456 A1 | 11/2003 | Lipchitz et al. |
| 2004/0059416 A1 | 3/2004 | Murray et al. |
| 2004/0073219 A1 | 4/2004 | Skiba et al. |
| 2004/0138705 A1 | 7/2004 | Heino et al. |
| 2004/0167519 A1 | 8/2004 | Weiner et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0327042 A1 | 12/2010 | Amid et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |
| 2012/0248171 A1 | 10/2012 | Bailly et al. |
| 2012/0316608 A1 | 12/2012 | Foley |
| 2013/0153627 A1 | 6/2013 | Euteneuer et al. |
| 2013/0153628 A1 | 6/2013 | Euteneuer |
| 2013/0158554 A1 | 6/2013 | Euteneuer et al. |
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |

(56) References Cited

FOREIGN PATENT DOCUMENTS

| | | |
|---|---|---|
| EP | 1559379 A1 | 8/2005 |
| EP | 2030576 A2 | 3/2009 |
| GB | 2154688 A | 9/1985 |
| GB | 2397240 A | 7/2007 |
| JP | 58188442 A | 11/1983 |
| JP | 2005506122 A | 3/2005 |
| JP | 2006515774 A | 6/2006 |
| WO | 85005025 A1 | 11/1985 |
| WO | 0176456 A2 | 10/2001 |
| WO | 200234140 A2 | 5/2002 |
| WO | 2003105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2011095890 A2 | 8/2011 |

OTHER PUBLICATIONS

Alexander et al., "Ligament and Tendon Repair with an Absorbable Polymer-Coated Carbon Fiber Stent," Bulletin of the Hospital; for Joint Diseases Orthopaedic Institute, vol. 46(2):155-173, 1986.

Bahler et al., "Trabecular Bypass Stents Decrease Intraocular Pressure in Cultured Human Anterior Segments," American Journal of Opthalmology, vol. 138(6):988-994, 2004.

Chamay et al., "Digital Contracture Deformity after Implantation of a Silicone Prosthesis: Light and Electron Microscopic Study," The Journal of Hand Surgery, vol. 3(3):266-270, 1978.

D'Ermo et al., "Our Results with the Operation of ab externo Trabeculotomym" Ophthalmologica, vol. 168, 347-355, 1971.

France et al., "Biomechanical Evaluation of Rotator Cuff Fixation Methods," The American Journal of Sports Medicine, vol. 17(2): 176-181,1989.

Goodship et al., "An Assessment of Filamentous Carbon Fibre for the Treatment of Tendon Injury in the Horse," The Veterinary Record, vol. 106, 217-221, 1980.

Hunter et al., "Flexor-Tendon Reconstruction in Severely Damaged Hands," The Journal of Bone and Joint Surgery (American Volume), vol. 53-A(5):329-358, 1971.

Johnstone et al., "Microsurgery of Schlemm's Canal and the Human Aqueous Outflow System," American Journal Opthalmology, vol. 76(6):906-917, 1973.

Kowalsky et al., "Evaluation of Suture Abrasion Against Rotator Cuff Tendon and Proximal Humerus Bone," Arthroscopy: The Journal of Arthroscopic and Related Surgery, vol. 24(3): 329-334, 2008.

Lee et al., "Aqueous-venous Shunt and Intraocular Pressure. Preliminary Report of Animal Studies," Investigative Opthalmology, vol. 5(1):59-64, 1966.

Mäepea et al., "The Pressures in the Episcleral Veins, Schlemm's Canal and the Trabecular Meshwork in Monkeys: Effects of Changes in Intraocular Pressure," Exp. Eye Res., vol. 49, 645-663, 1989.

Nicolle et al., "A Silastic Tendon Prosthesis as an adjunct to Flexor Tendon Grafting: An Experimental and Clinical Evaluation," British Journal of Plastic Surgery, vol. 22, Issues 3-4, 224-236, 1969.

Rubin et al., "The Use of Acellular Biologic Tissue Patches in Foot and Ankle Surgery," Clinics in Podiatric Medicine and Surgery, vol. 22, 533-552, 2005.

Schultz, "Canaloplasty Procedure Shows Promise for Open-angle Glaucoma in European Study," Ocular Surgery News, pp. 34-35, 2007.

Spiegel et al., "Schlemm's Canal Implant: A New Method of Lower Intraocular Pressure in Patients with POAG?" Opthalmic Surgery and Lasers, vol. 30(6): 492-494, 1999.

Stetson et al., "Arthroscopic Treatment of Partial Rotator Cuff Tears," Operative Techniques in Sports Medicine, vol. 12, Issue 2, pp. 135-148, 2004.

Valdez et al., "Repair of Digital Flexor Tendon Lacerations in the Horse, Using Carbon Fiber Implants," JAVMA, vol. 177(5): 427-435, 1980.

* cited by examiner

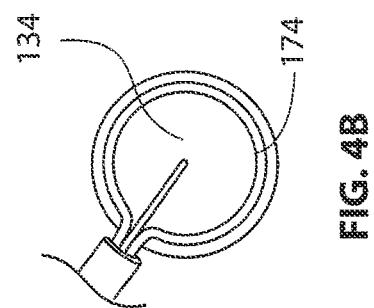
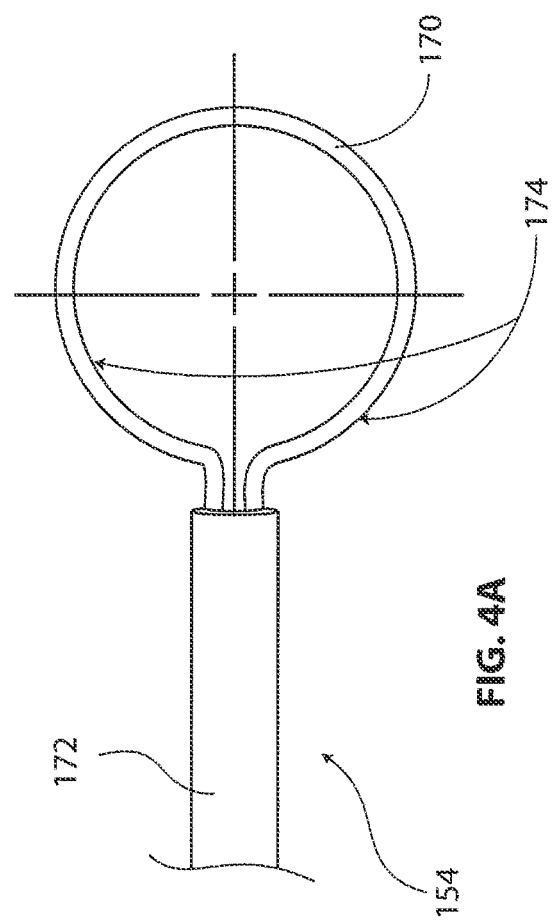

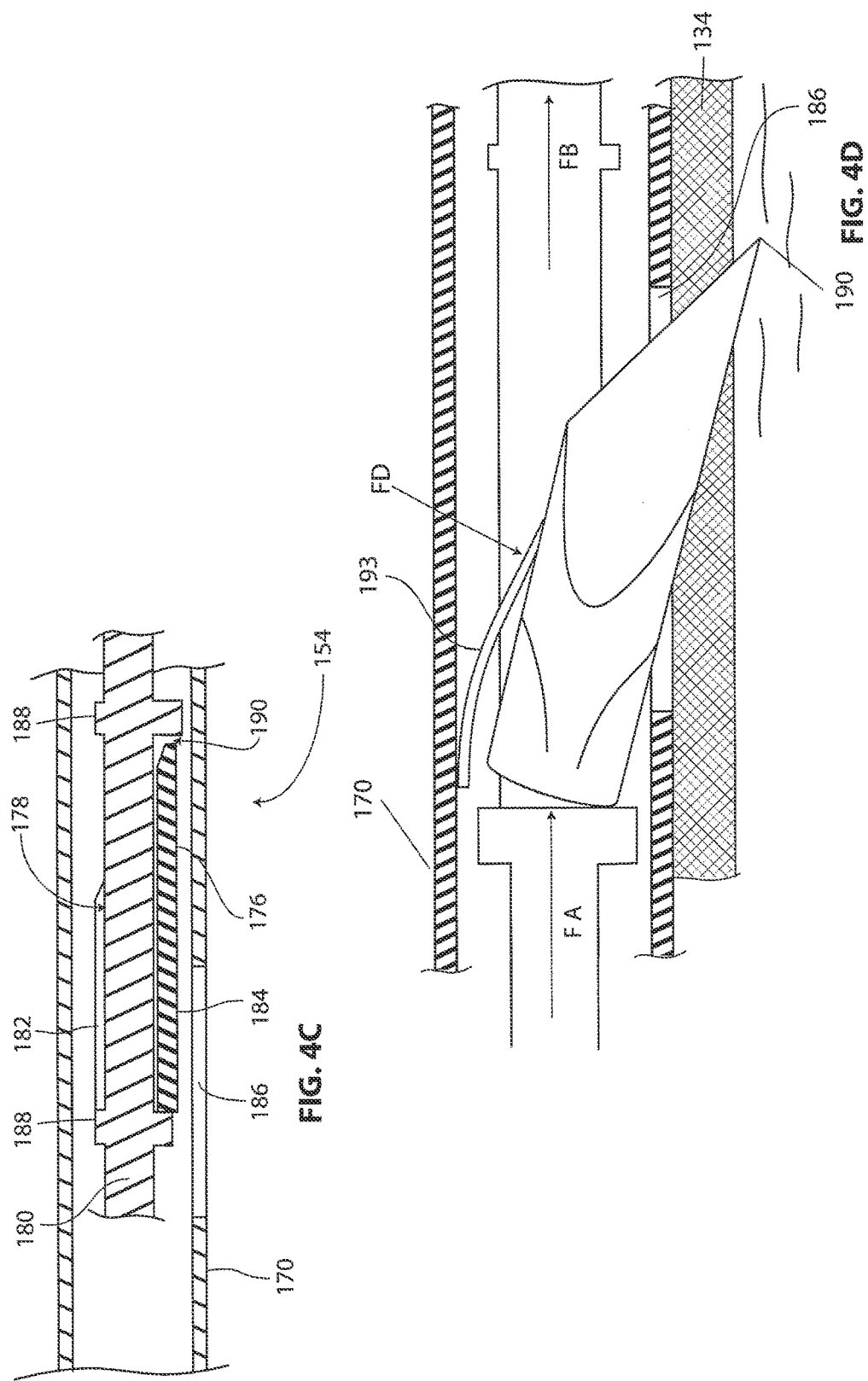

MEDICAL DEVICE DELIVERY SYSTEM AND METHOD

CROSS REFERENCE TO RELATED APPLICATIONS

This application is a continuation of U.S. application Ser. No. 12/729,029 filed on Mar. 22, 2010, which claims benefit to U.S. Provisional Patent Application No. 61/162,234, filed on Mar. 20, 2009, which is related to U.S. patent application Ser. No. 12/684,774, filed on Jan. 8, 2010. The disclosures of each of which are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to orthopedic medicine and surgery. More particularly, the present invention relates to methods and apparatus for delivery and fixation of medical devices, such as for treating articulating joints.

BACKGROUND OF THE INVENTION

The shoulder joint is found where the head of the humerus mates with a shallow depression in the scapula. The movement of the humerus relative to the scapula is controlled by a number of muscles including: the deltoid, the supraspinatus, the infraspinatus, the subscapularis, and the teres minor. Various patterns of activating these muscles create various rotational moments because the shoulder joint has no fixed axis. The tendons linking the supraspinatus, the infraspinatus, the subscapularis, and the teres minor to the humerus are typically referred to as the rotator cuff tendons. Some studies suggest that 85% of people over the age of 65 have some degree of rotator cuff damage. This damage may include thinning, fraying, and/or tearing of the rotator cuff tendons. Various factors may contribute to this rotator cuff damage. These factors include aging, overuse of the shoulder, and wearing of the tendons. Wearing of the tendons can occur, for example, when the rotator cuff tendons rub against a bone (e.g., the acromium of the scapula).

SUMMARY OF THE INVENTION

In accordance with various aspects of the present disclosure, a tendon repair implant and delivery system is provided that, in some embodiments includes a guide member having a temporary fixation member disposed adjacent to or on a distal end thereof. In some embodiments, the temporary fixation member is disposed proximate the distal end of the guide member. The guide member can be arthroscopically inserted to an implantation site and temporarily fixed at the site. A tendon repair implant including a sheet-like structure disposed in a collapsed configuration can be disposed over the guide member for slidable positioning to a target site.

The tendon repair implant can be pleat folded to the collapsed configuration and upon delivery to the target site assume an expanded shape.

The temporary fixation member can include a projection for piercing a tendon to provide a fixed target site for delivery of the tendon repair implant. The fixation member can also include a retractable barb for temporarily fixing the fixation member to the tendon. Alternatively, the temporary fixation member can include a threaded projection.

In some embodiments, the system of the present invention can include a tendon repair implant delivery tool which assists in placing and affixing the tendon repair implant to the tendon. The tendon repair implant delivery tool can include a support ring tube defining a lumen within which is disposed an anchor. Further, a pull wire is disposed within the lumen defined by the support ring tube and extends through a channel defined by the anchor. The pull wire can include a flange adjacent a proximal end of the anchor with the flange having a diameter greater than a width of the channel such that force applied to the pull wire causes the flange to deploy the anchor into adjacent tissue.

In some embodiments, the present invention also includes a method for positioning a tendon repair implant to overlay at least a portion of a supraspinatus tendon in the shoulder of a patient. The method includes providing an implant delivery device including a guide member having a temporary fixation member thereon which is then positioned with a distal portion of the guide member adjacent a bursal side of the supraspinatus tendon at a target site. The guide member is temporarily fixed to target site with the temporary fixation member. The tendon repair implant is advanced over the guide member for delivering the tendon repair implant to the target site and fixed to the supraspinatus tendon. The guide member is then removed from the target site. In some exemplary methods, the distal portion of the guide member is inserted from the front or back of the patient to a position adjacent the supraspinatus tendon. The guide member may be oriented so that it is generally parallel or tangent to an outer surface of the supraspinatus tendon.

BRIEF DESCRIPTION OF THE DRAWINGS

FIG. 4A is a top view of anchor delivery device.

FIG. 4B is a plan view showing a support ring of anchor delivery device overlaying a tendon repair implant.

FIG. 4C is a cross-sectional view of an anchor delivery device.

FIG. 4D is an additional cross-sectional view of the anchor delivery device shown in FIG. 4C.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Related U.S. application Ser. No. 12/684,774 filed Jan. 8, 2010 and entitled Impantable Tendon Protection System and Related Methods, provides an example of a medical device that may be delivered into a patient's shoulder joint through a cannula. During such an arthroscopic procedure, a surgeon's field of view through the cannula or arthroscope is typically very short. Accordingly, it can be difficult to accurately locate a target site for permanently implanting or temporarily placing such a medical device. Further, once a device is placed adjacent the target site and/or unfurled, many or all of the landmarks used by the surgeon to locate the target sight may be obscured. In the particular situation of the device being implanted as described in the above application, the target site may be spherically shaped and comprise slippery tissue, making placement of the implant even more difficult.

During such a delivery procedure, it may be desirable to first affirmatively locate the target site to which the medical device will be attached, and temporarily attach a locating guide to the target site to aid in delivering the medical device, according to aspects of the present detailed description. Once the medical device is attached to the target site, the located guide may be detached and removed. While the descriptions below and associated drawings refer to implanting a tendon protection device in a shoulder joint, in particular a sheet-like structure or disk-like structure, the system and method described herein and modified versions thereof may also be used to aid in temporarily or permanently placing other devices in other locations within a patient.

Figure 1B:
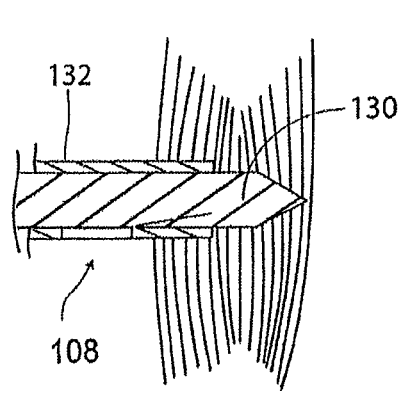
FIG. 1B and FIG. 1C are cross-sectional views illustrating two states of an exemplary temporary fixation mechanism.
Figure 1C:
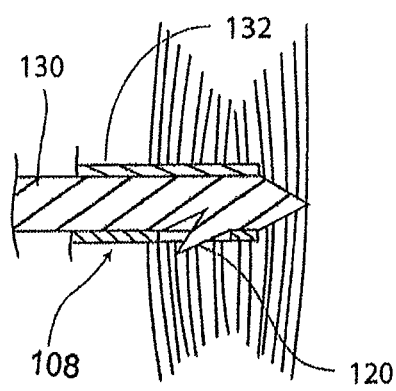
Figure 1A:
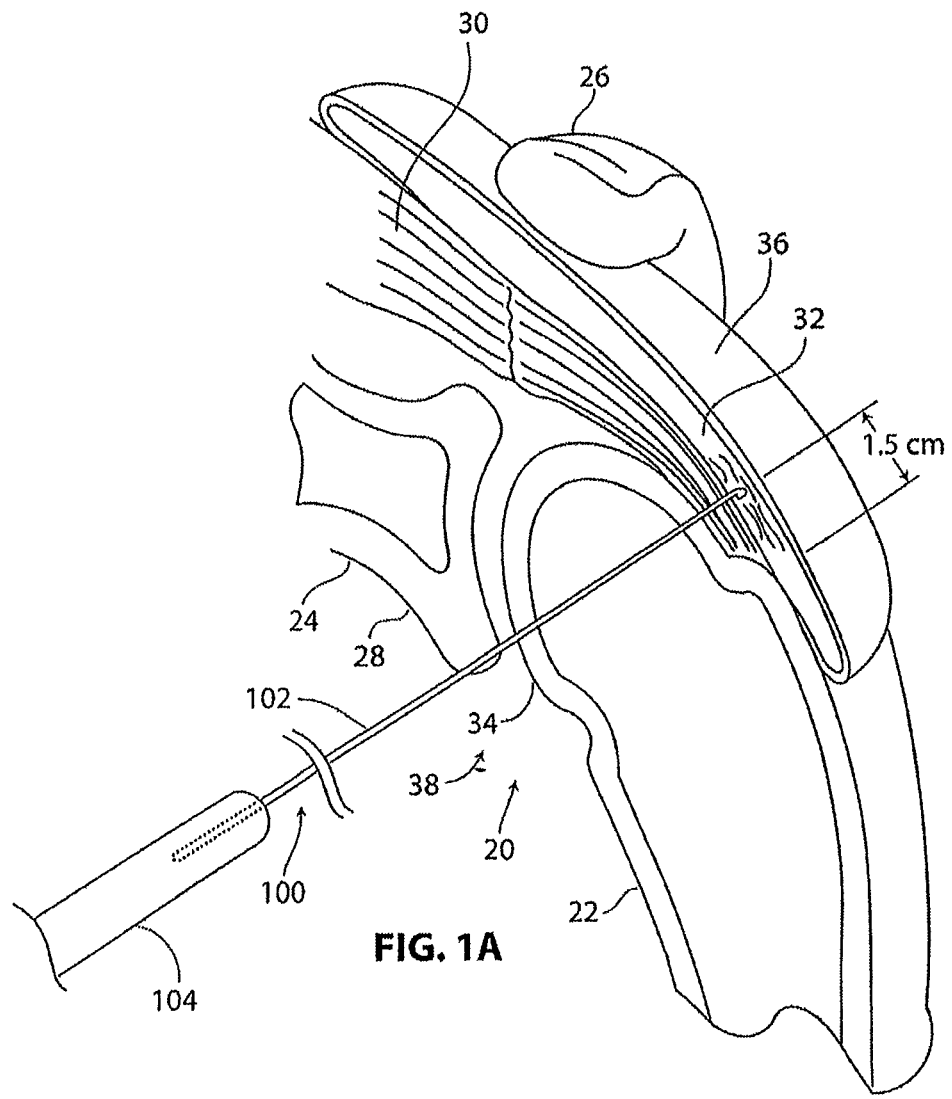
FIG. 1A is an isometric view of a shoulder including a humerus and a scapula.

FIG. 1A is an isometric view of a shoulder 20. Shoulder 20 includes a humerus 22 and a scapula 24. Scapula 24 comprises an acromium 26 and a glenoid fossa 28. The movement of humerus 22 relative to scapula 24 is controlled by a number of muscles including: the deltoid, the supraspinatus, the infraspinatus, the subscapularis, and the teres minor. For purposes of illustration, only the supraspinatus 30 is shown in FIG. 1. With reference to FIG. 1, it will be appreciated that a distal tendon 32 of the supraspinatus 30 meets humerus 22 at an insertion point In FIG. 1, a head 34 of humerus 22 is shown mating with glenoid fossa 28 of scapula 24 at a glenohumeral joint 38. In FIG. 1, a subacromial bursa 36 is shown extending between acromium 26 of scapula 24 and head 34 of humerus 22. Subacromial bursa 36 is shown overlaying supraspinatus 30 in FIG. 1. Subacromial bursa 36 is one of over one hundred and fifty bursae found the human body. Each bursa comprises a fluid filled sac. The presence of these bursae in the body reduces friction between bodily tissues. Injury and/or infection of the bursa can cause it to become inflamed. This condition is sometimes referred to as bursitis.

A locating guide 100 is also shown in FIG. 1. Locating guide 100 comprises a shaft 102 having a proximal end and a distal end. A handle 104 is fixed to the proximal end of shaft 102. In FIG. 1, a distal portion of shaft 102 is shown extending into an anterior side of shoulder 20 from a location in the front of the patient. The distal portion of shaft 102 may be inserted into the shoulder so that the longitudinal axis of the shaft extends generally parallel or tangent to an outer surface of a rotator cuff tendon (e.g., a supraspinatus tendon). This allows maneuvering the distal end of the shaft 102 to a target site for placing the tendon repair implant. In the exemplary embodiment of FIG. 1, shaft 102 may be moved in a generally posterior direction as the distal end of shaft 102 is advanced into the anterior side of shoulder 20. Shaft 102 may be advanced in other directions to insert the distal portion of shaft 102 without deviating from the spirit and scope of this detailed description. In some cases, for example, shaft 102 may be moved in a generally anterior direction as the distal end of shaft 102 is advanced into the posterior side of shoulder 20. Shaft 102 may also be moved in a generally superior or inferior direction as the distal end of shaft 102 is advanced into shoulder 20 in some cases. In some useful embodiments, locating guide 100 includes a temporary fixation mechanism proximate the distal end of shaft 102. A method in accordance with the present detailed description may include temporarily fixing the distal end of a shaft to a target site and advancing a tendon repair implant, which can include a sheet-like structure or tendon disk, over the shaft for delivering the implant to the target site.

FIG. 1B and FIG. 1C are cross-sectional views illustrating two states of an exemplary temporary fixation mechanism 108. In FIG. 1B, temporary fixation mechanism 108 is shown in a retracted state. In FIG. 1C, temporary fixation mechanism 108 is shown in a fixing state.

Shaft 102 of locating guide 100 comprises core wire 130 and a guide sheath 132. With reference to FIG. 1C, it will be appreciated that locating guide 100 includes a selectively deployable barb 120. In the embodiment of FIG. 1, barb 120 is biased to extend away from a longitudinal axis of core wire 130 as shown in FIG. 1C. In the embodiment of FIG. 1B, however, guide sheath 132 is urging barb 120 toward the longitudinal axis of core wire 130. In FIG. 1C, barb 120 is shown extending through an aperture defined by the wall of guide sheath 132. In one exemplary method of use, the distal end of shaft 102 is positioned adjacent a target site and inserted into the tendon tissue. The barb 120 is then deployed by moving guide sheath 132 longitudinally which temporarily affixes the locating guide 100 to the tendon for providing a track to deliver the tendon repair implant. When implantation is complete, the guide sheath 132 can be returned to its original position which urges the barb 120 against the core wire and releases the tendon. In an alternative embodiment (not shown), a helical screw tip may be employed on the distal end of core wire 130 to temporarily secure guide 100 to the tissue with a twisting motion of core wire 130. The temporary fixation structure can also comprise a projection that inserts into the tendon and holds or fixes a lateral position but can be released from the position by lifting the projection out of the tendon. A suture passed through the tendon may also be used to secure guide 100.

Figure 2:
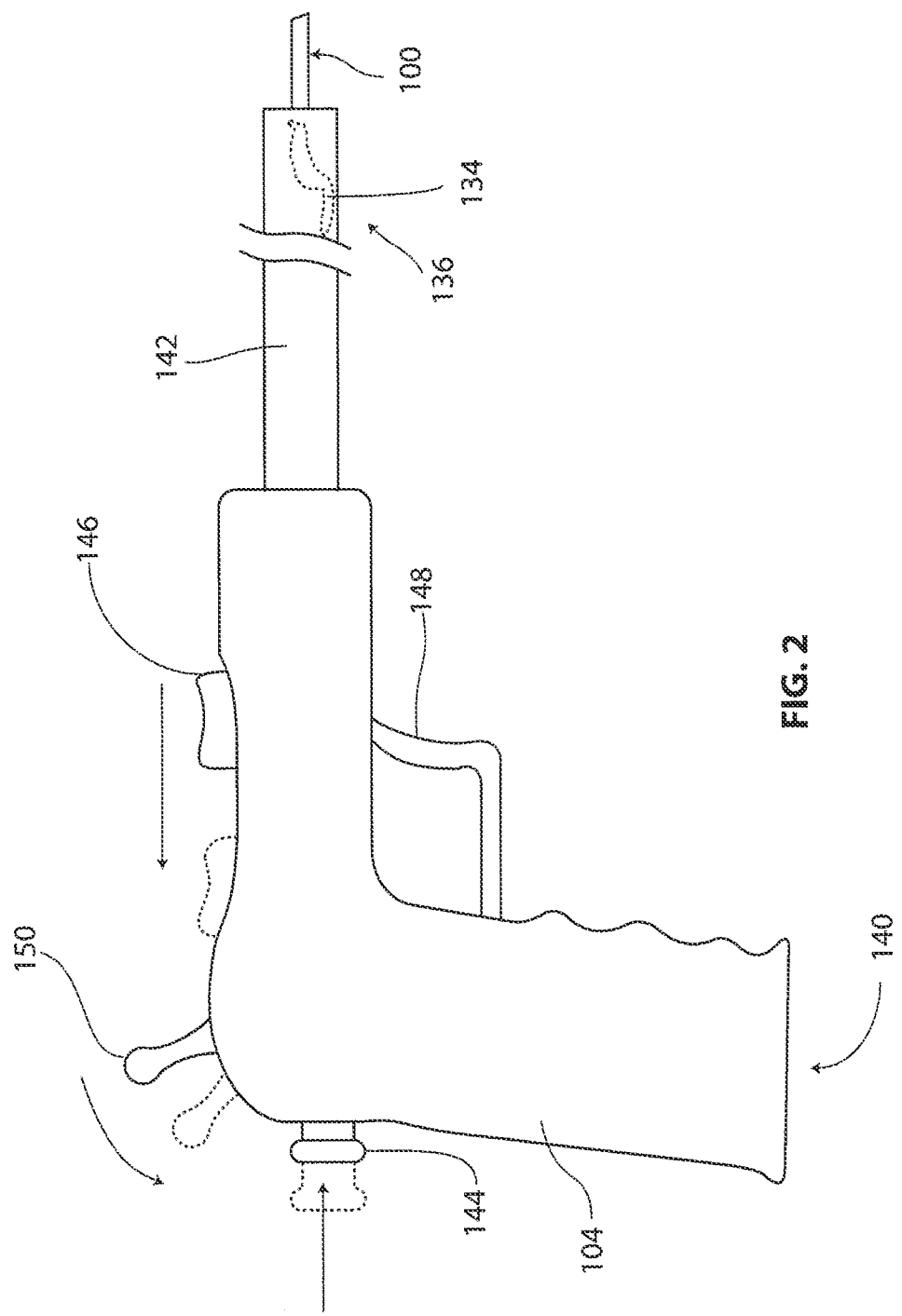
FIG. 2 is a plan view of an exemplary tendon repair implant delivery system.

FIG. 2 is a plan view of an exemplary tendon repair implant delivery system 140. The tendon repair implant can be a sheet-like or disk-like structure that overlays a portion of a tendon when implanted. In the embodiment of FIG. 2, tendon repair implant delivery system 140 comprises a delivery system sheath 142 and a handle 104. In the exemplary embodiment of FIG. 2, handle 104 has a pistol grip shape. It will be appreciated that handle 104 may have various shapes in addition to the exemplary shape shown in FIG. 2.

In the embodiment of FIG. 2, a tendon repair implant which comprises a sheet-like or disk-like structure 134 is disposed inside a distal portion 136 of delivery system sheath 142. Tendon repair implant delivery system 140 may be used to deploy tendon repair implant 134 within the body of a patient. Some methods in accordance with this description include attaching the implant to a tendon using a plurality of anchors. Tendon repair implant delivery system 140 may include an anchor delivery device for this purpose. In some useful embodiments, the anchor delivery device is capable of delivering a plurality of anchors for attaching the tendon repair implant to the tendon.

Tendon repair implant delivery system 140 may be used to perform various functions including deploying a sheet-like or disk-like structure within the body of a patient and anchoring the structure to a tendon. Tendon repair implant delivery system 140 includes a plurality of controls that may be used on conjunction with the various functions that can be performed using delivery system 140. The controls of delivery system 140 include a knob 144, a slide button 146, a trigger 148, and a toggling lever 150.

In the embodiment of FIG. 2, the position of delivery system sheath 142 may be altered by moving slide button 146 which is mechanically linked internally to delivery system sheath 142. Two positions of slide button 146 are shown in FIG. 2. In FIG. 2, a first position is shown with solid lines and a second position is shown with dashed lines. When slide button 146 is in the first position, implant delivery sheath will assume the advanced position shown in FIG. 2. When slide button 146 is in the second position, delivery system sheath 142 will assume a retracted position.

Knob 144 of implant delivery system 140 may be used to operate a locating guide 100. For example, knob 144 may be used to actuate a temporary fixation mechanism of locating guide 100. Knob 144 may cause the temporary fixation mechanism of locating guide 100 to alternate between the retracted state and the fixing state. When the temporary fixation mechanism is in the fixing state, it will selectively fix the distal end of locating guide 100 to a target site. For example, knob 144 may be mechanically connected to sheath 132, depicted in FIG. 1B such that actuating knob 144 results in longitudinal movement of sheath 132 to deploy or retract the barb as necessary to temporarily fix the distal end of the location member.

Implant delivery system 140 also includes a toggling lever 150. A support ring sheath of implant delivery system 140 may be advanced and retracted using toggling lever 150. Toggling lever 150 may be moved between a first position and a second position. In FIG. 2, the first position of toggling lever 150 is shown with solid lines and the second position of toggling lever 150 is shown with dashed lines.

When the support ring sheath is retracted, support ring tube will form a support ring. In some embodiments, a plurality of anchors are disposed inside the support ring tube. For example, six anchors may be evenly spaced along the support ring tube. In the embodiment of FIG. 2, trigger 148 may be used to dispense the anchors. In some embodiments, one anchor will be dispensed each time trigger 148 is actuated. In other embodiments, two or more anchors will be dispensed each time trigger 148 is actuated.

Figure 3:
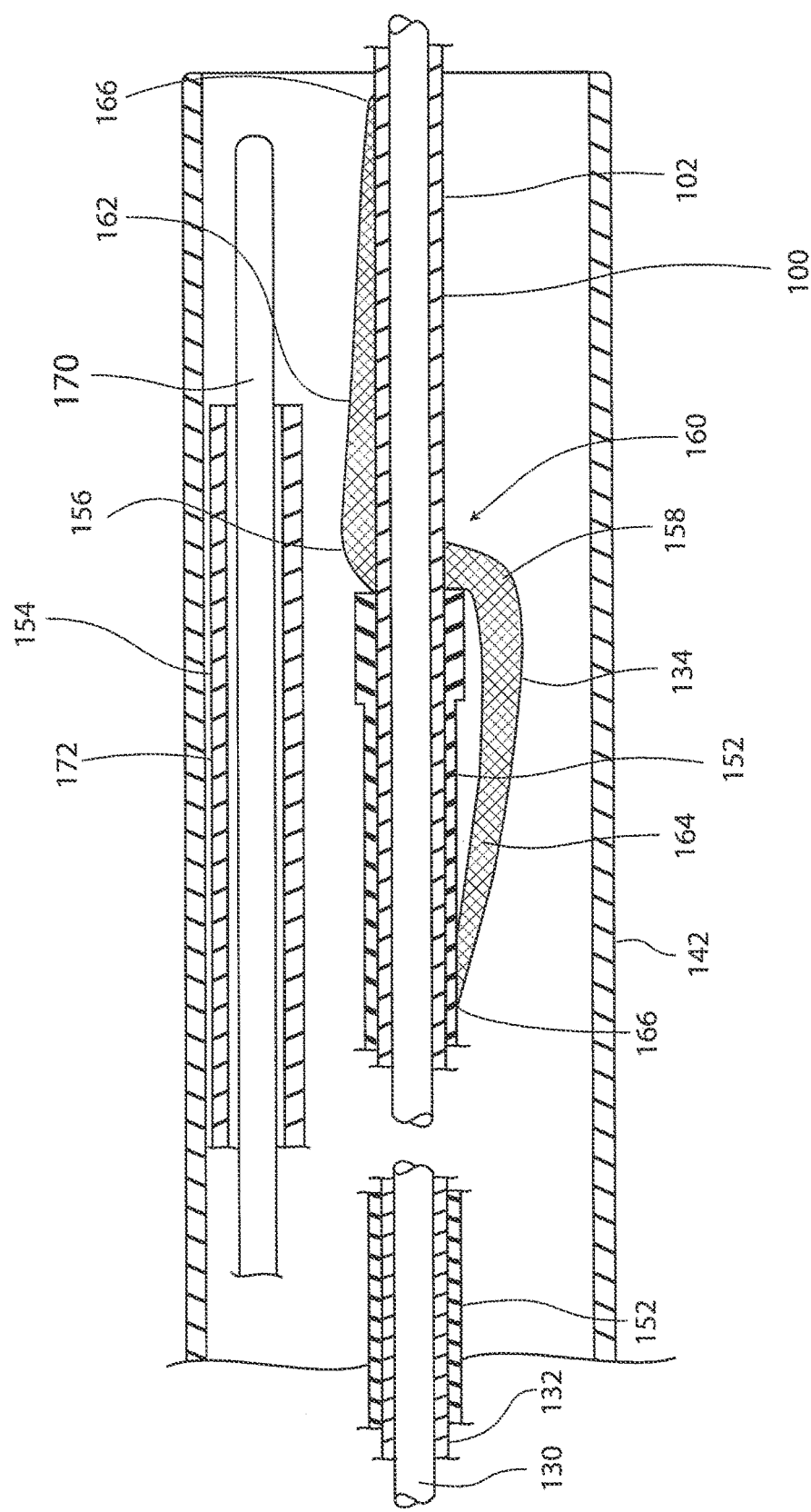
FIG. 3 is a cross-sectional view illustrating a distal portion of an exemplary tendon repair implant delivery system.

FIG. 3 is a cross-sectional view further illustrating a distal portion 136 of delivery system sheath 142. In FIG. 3, a tendon repair implant 134 can be seen residing inside a lumen defined by delivery system sheath 142. In the embodiment of FIG. 3, a locating guide 100, an implant push rod 152, and an anchor delivery device 154 are also disposed in the lumen defined by delivery system sheath 142.

Tendon repair implant 134 of FIG. 3 comprises a first lateral fold 156 and a second lateral fold 158. An intermediate portion 160 of tendon repair implant 134 is disposed between first lateral fold 156 and second lateral fold 158. With reference to FIG. 3, it will be appreciated that a shaft 102 of locating guide 100 extends through a hole in intermediate portion 160 of tendon repair implant 134.

In FIG. 3, a distal portion 162 of tendon repair implant 134 can be seen extending between first lateral fold 156 and an outer edge 166 of tendon repair implant 134. A proximal portion 164 of tendon repair implant 134 can be seen extending between second lateral fold 158 and outer edge 166 of tendon repair implant 134 in FIG. 3. Tendon repair implant 134 may also include a plurality of longitudinal folds (not visible in FIG. 3). For example, tendon repair implant 134 may be folded into a pleated shape including a plurality of longitudinal folds. In some embodiments, the tendon repair implant is folded or otherwise compacted to a collapsed configuration prior to insertion to the target or implant site. When properly positioned at the target site the tendon repair implant is reconfigured to an open or non-collapsed configuration to overlay at least a portion of the tendon. The tendon repair implant may be self-expanding such that when the implant is extended outside the sheath of the delivery system, it unfurls or expands to an open or sheet-like configuration.

In the embodiment of FIG. 3, locating guide 100 comprises a shaft 102. Shaft 102 comprises a guide sheath 132 disposed about core wire 130. In the embodiment of FIG. 3, an implant push rod 152 is disposed about guide sheath 132 of shaft 102. Implant push rod 152 may by used to urge tendon repair implant 134 distally along shaft 102 of locating guide 100.

In the embodiment of FIG. 3, an exemplary anchor delivery device 154 is disposed in the lumen defined by delivery system sheath 142. Anchor delivery device 154 comprises a support ring tube 170 and a support ring sheath 172 that is disposed about support ring tube 170. Support ring tube 170 is biased to form a support ring when support ring sheath 172 is in a retracted position. Support ring tube 170 assumes a contracted shape when support ring tube 170 is retracted into a lumen defined by support ring sheath 172. The operation of anchor delivery device 154 may be further explained with reference to the next figure.

FIG. 4 includes a plurality of additional views further illustrating anchor delivery device 154 shown in the previous figure. FIG. 4A is a top view of anchor delivery device 154. In the embodiment of FIG. 4A, support ring tube 170 is forming a support ring 174. Support ring 174 of FIG. 4A comprises a portion of support ring tube 170 that is extending beyond support ring sheath 172. In the embodiment of FIG. 4B, support ring tube 170 will be urged to assume a contracted shape when support ring tube 170 is retracted into a lumen defined by support ring sheath 172.

FIG. 4B is a plan view showing support ring 174 of anchor delivery device 154 overlaying a tendon repair implant 134. In some exemplary methods in accordance with the present description, support ring 174 is used to hold tendon repair implant 134 in intimate contact with a tendon. Support ring 174 of FIG. 4A comprises a portion of support ring tube 170 that is extending beyond support ring sheath 172. A shaft 102 of a locating guide 100 can be seen extending through a hole in tendon repair implant 134 in FIG. 4B.

FIG. 4C is a cross-sectional view of anchor delivery device 154. In some embodiments, anchor delivery device 154 comprises a plurality of anchors 176 that can be used to fix an implant to a tendon. One anchor 176 is visible in FIG. 4C. The anchor can be a blind anchor that is inserted into the tendon on the bursal side. In the embodiment of FIG. 4C, anchor 176 defines a channel 178. In FIG. 4C, a pull wire 180 can be seen extending through channel 178. A top surface 182 of anchor 176 and a bottom surface 184 of anchor 176 are both visible in FIG. 4C. Top surface 182 defines an open side of channel 178.

Anchor 176 and pull wire 180 are both disposed inside a lumen defined by a support ring tube 170. The wall of support ring tube 170 defines a plurality of apertures 186.

Each anchor 176 of anchor delivery device 154 may be selectively urged through an aperture 186 to anchor an implant to a tendon.

With reference to FIG. 4C, it will be appreciated that pull wire 180 has a plurality of flanges 188. In FIG. 4C, a flange 188 can be seen contacting a proximal end of anchor 176. Flange 188 and pull wire 180 may apply force to anchor 176. For example, force from pull wire 180 and flange 188 may be used to urge a distal point 190 of anchor 176 through an implant and into a tendon.

FIG. 4D is an additional cross-sectional view of anchor delivery device 154. In FIG. 4D, anchor 176 is shown extending through an aperture 186 defined by the wall of support ring tube 170. In the embodiment of FIG. 4D, an anchor deflector 193 is applying a deflecting force to anchor 176. This deflecting force is represented with an arrow FD in FIG. 4D. In FIG. 4D, an arrow FA is used to represent a force that flange 188 is applying to anchor 176. An additional arrow FB is also visible in FIG. 4D. Arrow FB represents a pulling force that is being applied to pull wire 180. In the embodiment of FIG. 4, distal point 190 of anchor 176 has penetrated the cuff of a tendon repair implant 134. Distal point 190 is shown residing in a tendon.

Figure 5:
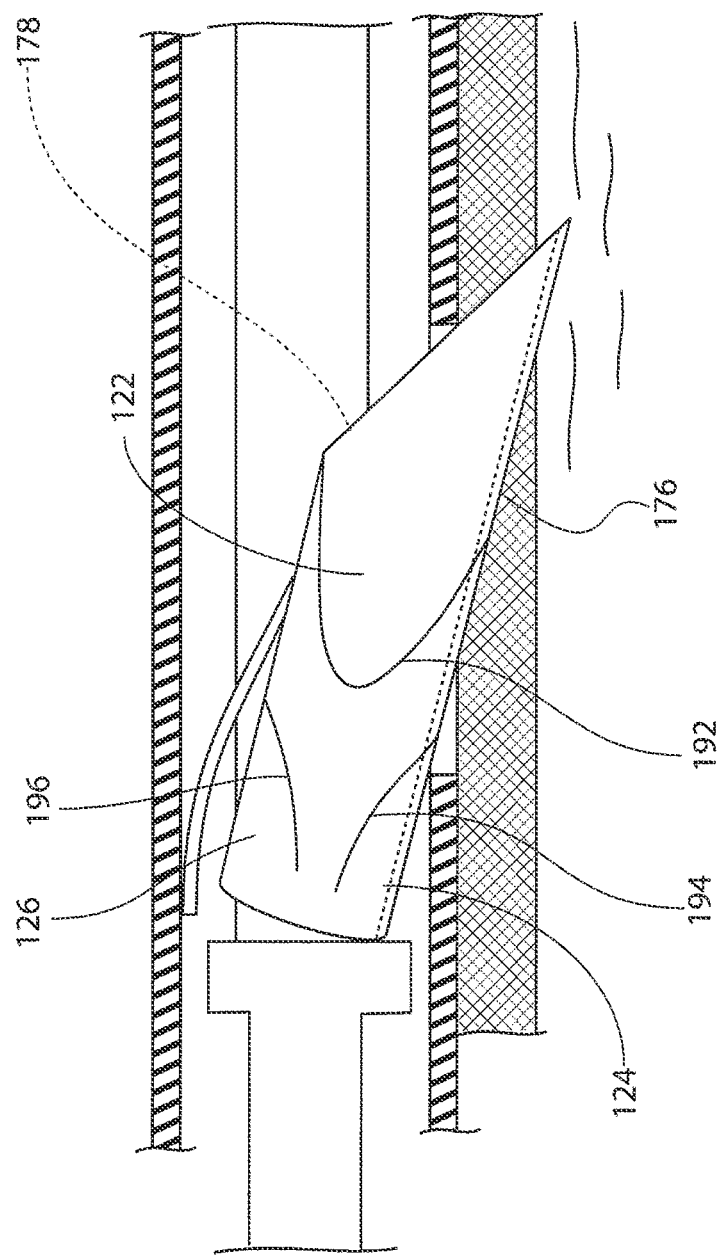
FIG. 5 is an enlarged view of an anchor shown in FIG. 4C.

FIG. 5 is an enlarged view of anchor 176 shown in the previous figure. With reference to FIG. 5, it will be appreciated that anchor 176 comprises a body 198 having a distal point 190. Body 198 of anchor 176 defines a channel 178. Body 198 includes a first notch 192, a second notch 194, and a third notch 196. First notch 192 defines a first barb 122 of anchor 176. Second notch 194 and third notch 196 define a second barb 124 and a third barb 126 respectively. The barbs of anchor 176 may expand outward once anchor 176 is deployed.

Figure 6:
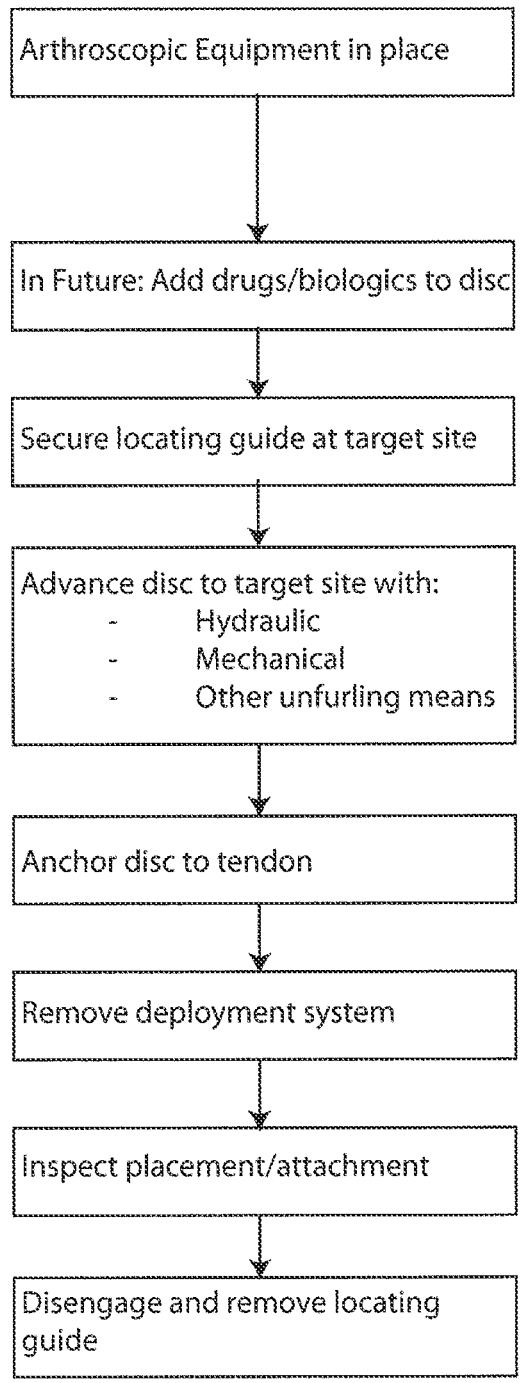
FIG. 6 is a flow chart describing a method for treating a patient.

FIG. 6 is a flow chart describing a method for treating a patient. A method in accordance with the present description may include accessing a target site in the body of a patient. In some applications, arthroscopic equipment may be used to access a joint (e.g., a shoulder joint) in the patient's body. The arthroscopic equipment may include, for example, a cannula. The cannula may be positioned so that the distal end of the cannula is inside the shoulder of the patient. The cannula defines a lumen. Various devices may be advanced through a proximal opening of the cannula and into the lumen defined by the cannula. The cannula then guides the device into the shoulder.

A method in accordance with the present detailed description may include anchoring the distal end of a guide shaft to a target site and advancing a tendon repair implant over the shaft for delivering the tendon repair implant to the target site. Some methods in accordance with this description include attaching the implant to a tendon using a plurality of anchors. An anchor delivery device may be used for this purpose. In some useful embodiments, the anchor delivery device is capable of delivering a plurality of anchors for attaching the implant to the tendon.

A therapeutic agent may be applied to the tendon repair implant prior to positioning at the target site. Therapeutic agents can include: drugs, anti-inflammatory agents, painkillers, antibiotics, proteins, hormones, growth factors, and growth factor sources. Growth factor sources may include, for example, platelets and platelet rich plasma (PRP). A tendon repair implant may contain calcium chloride for causing platelet aggregation, which will cause release of growth factors. Examples of growth factors that may be suitable in some applications include but are not limited to heparin binding growth factor ("HBGF"), platelet-derived growth factor ("PDGF"), transforming growth factor alpha or beta ("TGF-.alpha." or "TGF-.beta."), basic fibroblast growth factor ("bFGF"), epidermal growth factor ("EGF"), and vascular endothelial growth factor ("VEGF"). Examples of hormones that may be suitable in some applications include but are not limited to insulin, glucagon, and estrogen. It will be appreciated that therapeutic agents can be delivered to the target site apart from the tendon repair implant, either before or after placement of the implant.

While exemplary embodiments of the present invention have been shown and described, modifications may be made, and it is therefore intended in the appended claims to cover all such changes and modifications which fall within the true spirit and scope of the invention.

What is claimed is:

1. An implant delivery system comprising:
   a sheath member having a distal end and a proximal end, the sheath member extending along a longitudinal axis;
   a locating guide having a proximal end and a distal end and disposed at least partially within the sheath member;
   a tendon repair implant disposed within the sheath member, the tendon repair implant having a first side and a second side opposite the first side: and
   a support disposed at least partially within the sheath member; wherein the support frame assumes a compact configuration when disposed within the sheath member and assumes an expanded configuration when uncovered by the sheath member,
   wherein the support in the expanded configuration is configured to overlay and contact only the first side of the tendon repair implant to press the tendon repair implant against tissue,
   wherein the locating guide further comprises a temporary fixation mechanism disposed proximate the distal end of the locating guide, and
   wherein, when the support is in the expanded configuration, a distal portion of the locating guide extends through the tendon repair implant from the first side to the second side, such that the temporary fixation mechanism is positioned distal of the tendon repair implant to penetrate tissue.

2. The implant delivery system of claim 1, wherein in the expanded configuration the support lies in a plane parallel to the longitudinal axis.

3. The implant delivery system of claim 1, wherein the sheath member is retractable relative to the support to uncover the support.

4. The implant delivery system of claim 1, wherein the tendon repair implant is slidable relative to the locating guide.

5. An implant delivery system comprising:
   a sheath member having a distal end and a proximal end;
   a locating guide having a proximal end and a distal end and disposed at least partially within the sheath member;
   a tendon repair implant disposed within the sheath member, the tendon repair implant having a first side and a second side opposite the first side; and
   a support disposed at least partially within the sheath member, wherein at least a portion of the support assumes a compact configuration within the sheath member,
   wherein when the portion of the support in the compact configuration is uncovered by the sheath member, the support expands from the compact configuration to an expanded configuration, wherein the support in the expanded configuration is configured to overlay the tendon repair implant and contact only the first side of the tendon repair implant to press the tendon repair implant against tissue, wherein the locating guide comprises a temporary fixation feature disposed adjacent the locating guide distal end, the temporary fixation feature extends through the tendon repair implant from the first side to the second side such that the temporary fixation feature is positioned distal of the tendon implant to penetrate tissue when the support is in the expanded configuration.

6. The implant delivery system of claim 5, wherein the support resides within a support sheath, wherein the support sheath is disposed within the sheath member, and wherein the support assumes the expanded configuration when uncovered by both the sheath member and the support sheath.

7. The implant delivery system of claim 5, wherein the locating guide extends through a portion of the tendon repair implant.

8. The implant delivery system of claim 5, further comprising an implant push rod to advance the tendon repair implant distally through the sheath member.

9. The implant delivery system of claim 5, wherein the tendon repair implant is self-expanding.

* * * * *